United States Patent [19]
Coleman

[11] Patent Number: 5,955,735
[45] Date of Patent: Sep. 21, 1999

[54] APPARATUS AND METHOD FOR POSITIVELY IDENTIFYING SYNTHETIC SILICON CARBIDE GEMSTONES

[75] Inventor: Thomas G. Coleman, Pittsboro, N.C.

[73] Assignee: C3, Inc., Morrisville, N.C.

[21] Appl. No.: 08/939,346

[22] Filed: Sep. 29, 1997

[51] Int. Cl.⁶ .......................... G01N 21/87; G01R 31/00
[52] U.S. Cl. ...................... 250/372; 250/336.1; 356/30; 324/96; 324/133; 324/149
[58] Field of Search ................................. 250/336.1, 372, 250/365, 389; 324/71.1, 71.5, 96, 133, 149; 356/30

[56] References Cited

U.S. PATENT DOCUMENTS

| | | |
|---|---|---|
| 4,255,962 | 3/1981 | Ashman . |
| 5,093,576 | 3/1992 | Edmond et al. . |
| 5,536,943 | 7/1996 | Smith et al. . |
| 5,723,391 | 3/1998 | Hunter et al. .............................. 501/86 |

OTHER PUBLICATIONS

Dale M. Brown, et al. "Silicon Carbide UV Photodiodes." IEEE Transaction on Electron Devices, vol. 40. No. 2. pp. 325–333, Feb. 1993.

J. Edmund et al. "6H–Silicon Carbide Light Emitting Diodes and UV Photodiodes" (1997) Phys. Stat. Sol. (9) 162 pp. 481–491.

Primary Examiner—Constantine Hannaher
Assistant Examiner—Albert J. Gagliardi
Attorney, Agent, or Firm—Richard S. Faust

[57] ABSTRACT

A target gemstone is irradiated with ultraviolet energy while sensing the electrical potential across the gemstone. A silicon carbide gemstone will generate an electrical potential and, therefore, can be positively identified, as distinct from other gemstones such as diamond and cubic zirconia that do not produce a potential.

21 Claims, 6 Drawing Sheets

APPARATUS AND METHOD FOR POSITIVELY IDENTIFYING SYNTHETIC SILICON CARBIDE GEMSTONES

FIELD OF THE INVENTION

The invention relates to procedures and instruments for distinguishing between materials through nondestructive testing. More particularly, the invention relates to distinguishing between materials with similar visual appearance, e.g., gemstones of similar appearance. In preferred embodiments, the invention provides a reliable, nondestructive testing approach for positively identifying a gemstone as moissanite (silicon carbide), as distinct from diamond, cubic zirconia or other gemstone material.

BACKGROUND OF THE INVENTION

Dating from prehistoric times, diamond has had a mythical importance to many civilizations and, as a result, has one of the highest values of all naturally occurring materials. Diamond is, of course, a crystalline form of carbon whose beauty and value derive from its extraordinary hardness, toughness and high refractive index. It is primarily the refractive index that gives diamond its characteristic brilliance.

Simulated diamond materials have entered the marketplace with varying degrees of success. The most widely distributed simulated diamond material is cubic zirconia. While cubic zirconia usually can be distinguished from diamond through visual inspection by a qualified jeweler, a test comparing physical properties of cubic zirconia versus diamond is desirable to prevent improper identification of a gemstone. In this regard, cubic zirconia has a lower refractive index than diamond. Also, it is considerably softer, has a much higher density and has a significantly lower thermal conductivity. One relatively straightforward and reliable nondestructive test for distinguishing cubic zirconia from natural diamond is set forth in U.S. Pat. No. 4,255,962 which describes an apparatus including a thermal probe held in physical contact with the gemstone being tested, and associated circuitry for determining the thermal conductivity of the gemstone.

Recently, it has been discovered that single crystals of synthetic silicon carbide can be grown with desired color characteristics and thereafter faceted and polished into synthetic gemstones. These gemstones have extraordinary hardness, toughness, chemical and thermal stability, and a high refractive index that produces unparalleled brilliance.

Synthetic silicon carbide crystals can be grown in a wide range of colors and shades within each color by the appropriate selection of dopants and by varying the net doping densities. The silicon carbide crystals can also be grown colorless. Thus, silicon carbide crystals offer the potential to be faceted and polished into gemstones of many various appearances, including that of diamond.

A comparison of certain important physical properties of diamond, silicon carbide and cubic zirconia is as follows:

| | Mohs Hardness | Refractive Index | Density (SG) | Thermal Conductivity (W/cm · K) |
|---|---|---|---|---|
| Natural Diamond | 10 | 2.42 | 3.5 | 6.6 |
| Silicon Carbide (6H polytype) | 9–9.25 | 2.69 | 3.2 | 4.9 |
| Silicon Carbide (4H polytype) | 9–9.25 | 2.71 | 3.2 | 4.9 |
| Cubic Zirconia | 7.75–8.5 | 1.98 | 5.8 | 0.02 |

Even for an experienced jeweler or diamond merchant, the difference between diamond and a colorless silicon carbide gemstone is difficult, if not impossible, to see with the naked eye. The skilled use of the usual optical tools employed in the industry still do not produce reliable results in distinguishing between the two materials. In fact, certified gemstone appraisers are known to have mistakenly identified silicon carbide as diamond. The differences that may appear in color are of no significance since silicon carbide gemstones may be produced in colorless form or with a slight tint. For example, a silicon carbide gemstone may be produced with the light shading of blue that is found in certain diamonds, including some of the rarest and most expensive diamonds, such as the Hope Diamond. As shown in the above table, the differences in hardness, refractive index, density and thermal conductivity between diamond and silicon carbide are not sufficiently great to form a basis for a reliable, easy to use testing procedure and apparatus that can be employed by typical jewelry stores and appraisers.

Other sophisticated laboratory tests might be considered for application to the problem of distinguishing silicon carbide gemstones from natural diamond gemstones. However, even many complicated and otherwise reliable techniques are limited in their application to this problem because silicon carbide can form in more than 150 different atomic arrangements (polytypes) each having different physical and electronic characteristics. In addition, the hexagonal polytypes of silicon carbide have properties that are different in each crystallographic plane. For instance, ultraviolet fluorescence of silicon carbide has little value because many silicon carbide polytypes (including 6H) do not fluoresce. Since a certain percentage of natural diamond also does not fluoresce, ultraviolet fluorescence cannot reliably distinguish between silicon carbide and diamond. Furthermore, spectrometry and x-ray techniques are not necessarily appropriate to the task because they are highly dependent on the skill of the operator and are far too complex and/or time-consuming and/or expensive to be employed on a routine basis in the tens of thousands of businesses that must now be concerned with distinguishing between diamond and silicon carbide gemstones.

With the advent of synthetic silicon carbide gemstones, and particularly colorless and lightly tinted silicon carbide gemstones, there has developed an acute need for a reliable and cost-effective procedure and apparatus for use by jewelry stores, appraisers and pawn shops to positively identify silicon carbide gemstones and thereby distinguish them from diamond, cubic zirconia and other gemstones, with the end goal of preventing intentional or unintentional misidentification of these gemstones.

SUMMARY OF THE INVENTION

The present invention, in its broadest sense, is an apparatus and method that permits one to positively identify a target gemstone as silicon carbide by sensing the electrical potential across the gemstone while it is being irradiated with ultraviolet energy. A silicon carbide gemstone will absorb ultraviolet energy and generate electron hole pairs therein that will be manifest as an electrical potential across the gemstone. Other gemstones, most notably diamond and cubic zirconia, will not generate a potential.

In one basic embodiment, the device of the invention includes means for sensing the electrical potential across a target gemstone that is irradiated with ultraviolet energy and means for generating an output that is a function of the sensed potential so that the stone may be positively identified as silicon carbide.

One preferred hand-held, battery powered solid state embodiment utilizes a light emitting diode (LED) ultraviolet emitting light source. This embodiment includes a pair of probes that contact the target gemstone. The probes are mounted to a pressure activated switch that activates the detector circuit. The electrical circuitry of this and other embodiments utilizes an operational amplifier and a visual or audible output device to generate an output that is a function of the electrical potential sensed by the probes.

BRIEF DESCRIPTION OF THE DRAWINGS

Some of the objects having been stated, other objects will appear as the description proceeds, when taken in connection with the accompanying drawings, in which.

DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
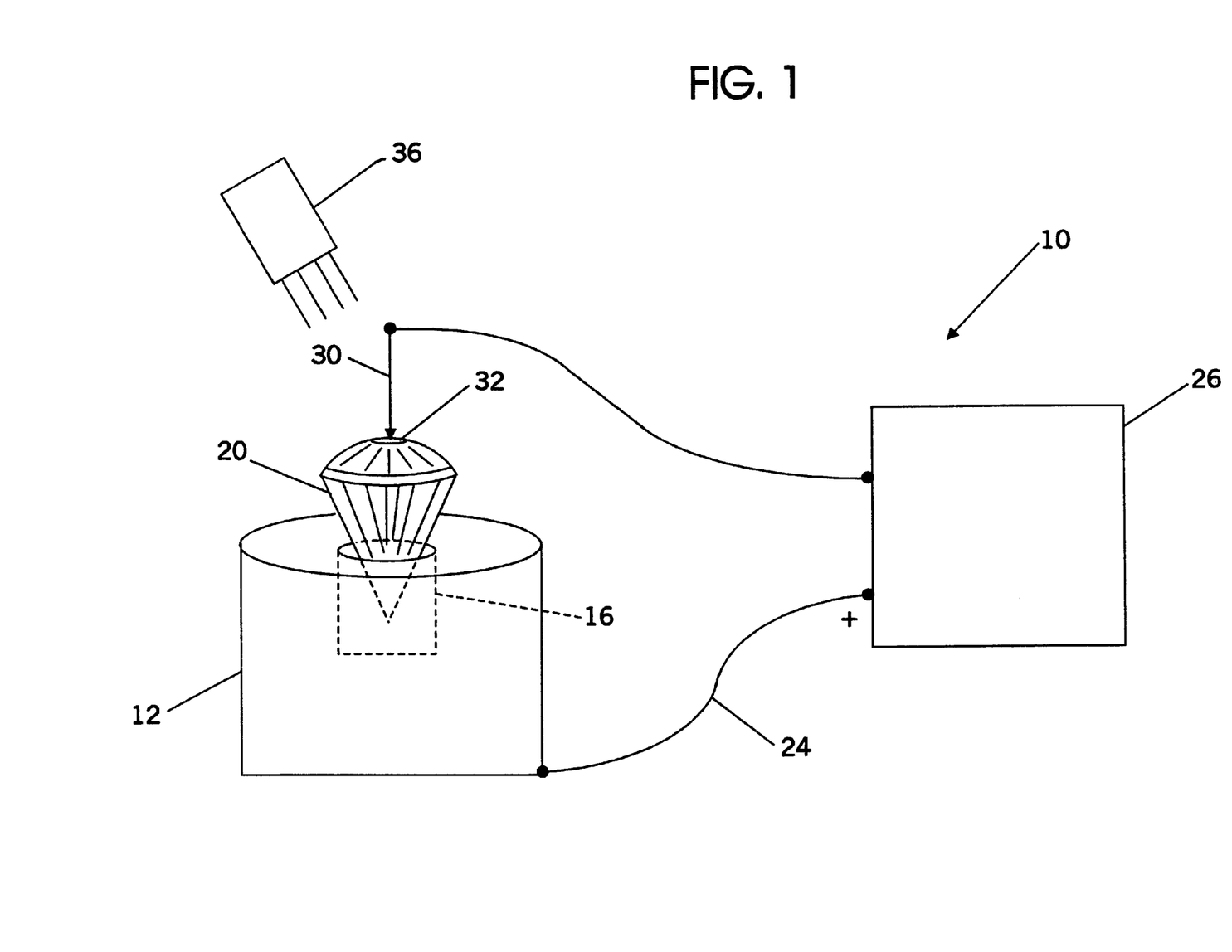
FIG. 1 is a diagrammatic view of one simplified embodiment of a device for positively identifying silicon carbide gemstones.

Referring to the drawings, and particularly to FIG. 1, there is shown a device 10 that will positively identify a target gemstone as silicon carbide. Device 10 includes a gem holder 12 formed of an electrically conductive material such as graphite. Gem holder 12 includes a recess 16 for holding a gem, such as round brilliant cut synthetic silicon carbide gemstone 20. An electrical lead 24 connects the gem holder 12 to a voltmeter 26, such as a digital voltmeter having 200 mv DC range and low drift characteristics. One acceptable voltmeter with this capability is a model no. 8060A voltmeter manufactured by John Fluke Mfg., Inc. of Everett, Wash., USA. A probe 30 is held in direct contact with the table 32 of gemstone 20. The probe is formed from palladium, brass, copper or other suitable conductor. A light source that emits ultraviolet energy, for example a 50 watt quartz halogen bulb 36, irradiates gemstone 20 with light containing ultraviolet energy. If the target gemstone is silicon carbide, a significant measurable electrical potential is sensed and an output that is a function of the sensed potential is displayed by the voltmeter to positively indicate whether the material of the target gemstone is or is not silicon carbide.

Device 10 was used to measure the potential across a number of representative gemstones while being irradiated by ultraviolet energy from the mentioned quartz halogen light source at a distance on the order of four inches. Table I, set forth below, identifies ten target gemstones and the voltage output associated with each gemstone while being irradiated.

TABLE I

| TARGET GEMSTONE | VOLTAGE OUTPUT (MILLIVOLTS) |
|---|---|
| A. 1.050 carat round brilliant synthetic silicon carbide 6H polytype, GIA color grade P, clarity #2, cut 3 PL, girdle diameter 6.9 mm | A. 1.8 |
| B. 2.11 carat round brilliant synthetic silicon carbide 6H polytype, light green color, girdle diameter 8.6 mm | B. 3.8 |
| C. 1.75 carat round brilliant synthetic silicon carbide 6H polytype, dark green color, girdle diameter 7.6 mm | C. 0.90 |
| D. 0.686 carat round brilliant synthetic silicon carbide 6H polytype, GIA color grade K, clarity #5, cut 5.A, finish 3, girdle diameter 6.1 mm | D. 1.91 |
| E. 0.803 carat round brilliant synthetic silicon carbide 6H polytype, GIA color grade O, clarity #5, cut 2, finish 2, girdle diameter 6.2 mm | E. 0.69 |
| F. 0.690 carat round brilliant synthetic silicon carbide 4H polytype, light blue color, clarity #3, cut 3B, yo/55, girdle diameter 6.0 mm | F 4.6 |
| G. 0.723 carat round brilliant synthetic silicon carbide 4H polytype, light blue color, clarity #4, cut 3, girdle diameter 6.1 mm | G. 17.3 |
| H. 0.46 carat round brilliant cut diamond, GIA color scale K, clarity 5I-2, cut 2, table diameter 5.19 mm | H. 0 |
| I. 0.5 carat round brilliant cut diamond, blue color | I. 0 |
| J. 1.905 carat round brilliant cut cubic zirconia, GIA color scale E, clarity 1, cut 5RB, finish 2, table diameter 6.4 mm | J. 0 |

It can be seen that in each instance the synthetic silicon carbide gemstone produced a significant electrical potential across the stone while being irradiated. The diamond and cubic zirconia gemstones produced no potential.

The present invention has its primary utility in connection with distinguishing between colorless gemstones such as diamond, cubic zirconia and synthetic silicon carbide. Synthetic silicon carbide gemstones that are colorless may have low to very low doping densities within the crystalline structure. However, other forms of synthetic silicon carbide gemstones, including gemstones intentionally doped for imparting a desired color, may have higher doping densities. In this regard, it has been found that the voltage output during irradiation of a synthetic silicon carbide gemstone varies somewhat with the doping density. However, within the range of doping densities believed to be suitable for both colorless and colored synthetic silicon carbide gemstone material, the present invention is fully operable.

Figure 2:
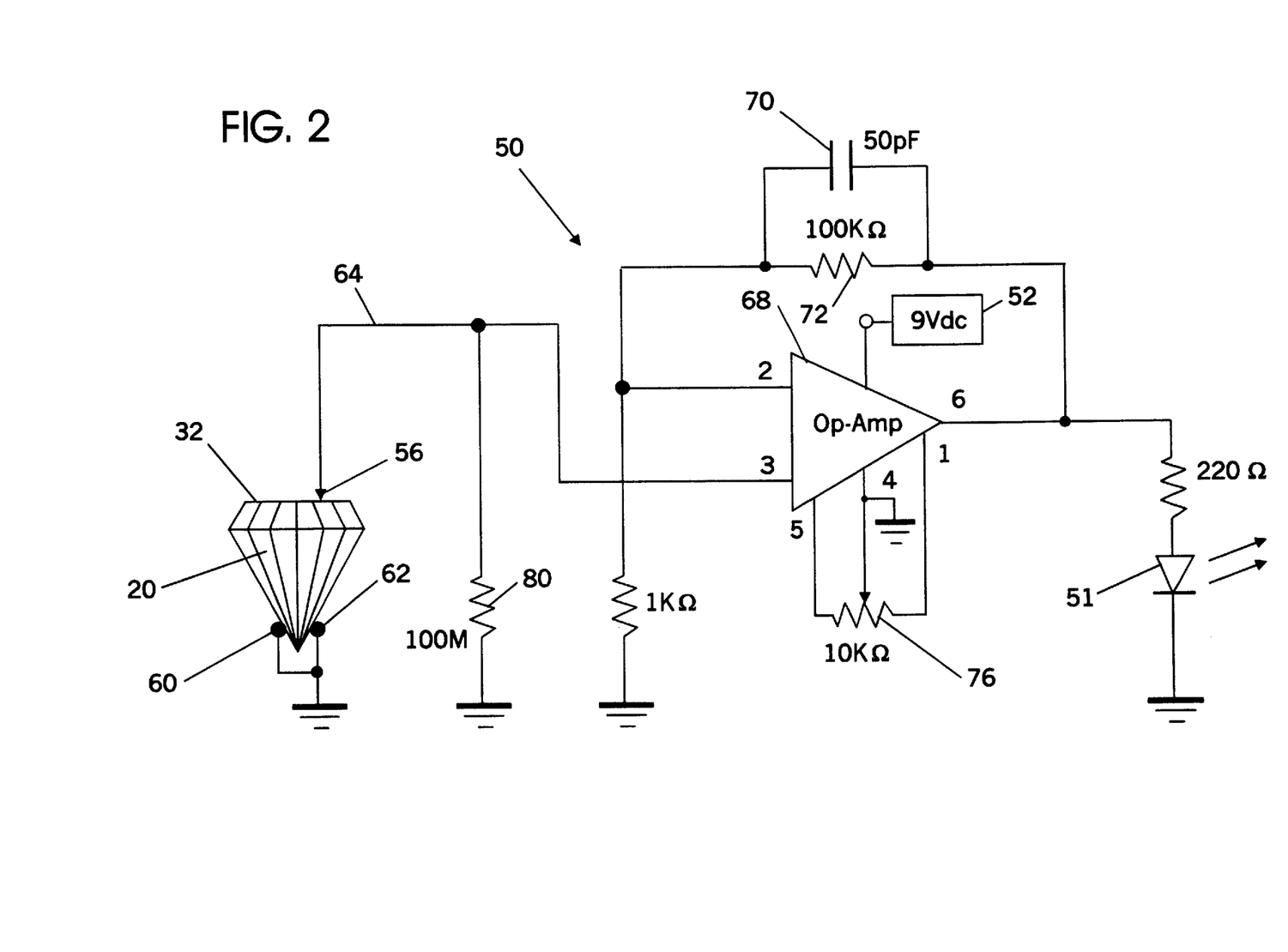
FIG. 2 is a schematic representation of one preferred form of the circuitry for a device of the invention shown in conjunction with a target gemstone that is supported by a grounded electrical contact structure and is contacted at its table by a single probe.

FIG. 2 schematically illustrates one preferred circuit 50 for use in a self-contained test device where the output is in the form of an LED 51 that glows to indicate a silicon carbide gemstone. FIG. 2 does not illustrate an ultraviolet emitting light source because the device of the invention, in its most basic form, does not necessarily require a light source if it is to be used in ambient light conditions containing sufficient ultraviolet energy, e.g. in certain sunlight conditions or artificial light conditions having sufficient ultraviolet energy. An ultraviolet emitting light source may be added to the circuitry of FIG. 2 by conventional connection to battery 52 including appropriate switching circuitry, an example of which will be discussed later in the specification.

Circuit 50 includes a probe 56 that is placed in contact with target gemstone 20, preferably at the gemstone table 32. The gemstone is supported by a grounded contact structure, for example a structure comprising multiple contacts 60, 62. An electrical connector 64 connects probe 56 to an operational amplifier 68 that is powered by battery 52. Voltage generated at a silicon carbide gemstone is a positive voltage to operational amplifier 68 at pin 3. Operational amplifier 68 serves to produce an output voltage at pin 6 that is amplified to provide a variable drive voltage to LED 51. In the illustrated embodiment, the amplification achieved by the amplifier circuitry is a 100× gain. Other components of the amplifier circuitry include a 50 pF capacitor 70 and a 100 K ohm resistor 72 in parallel that serve as feedback to set the gain of the amplifier. A 10 K resistor 76 serves as a null pod that sets the balance of operational amplifier 68. A 100 meg ohm resistor 80 serves to return all terminals of operational amplifier 68 to ground.

Figure 3:
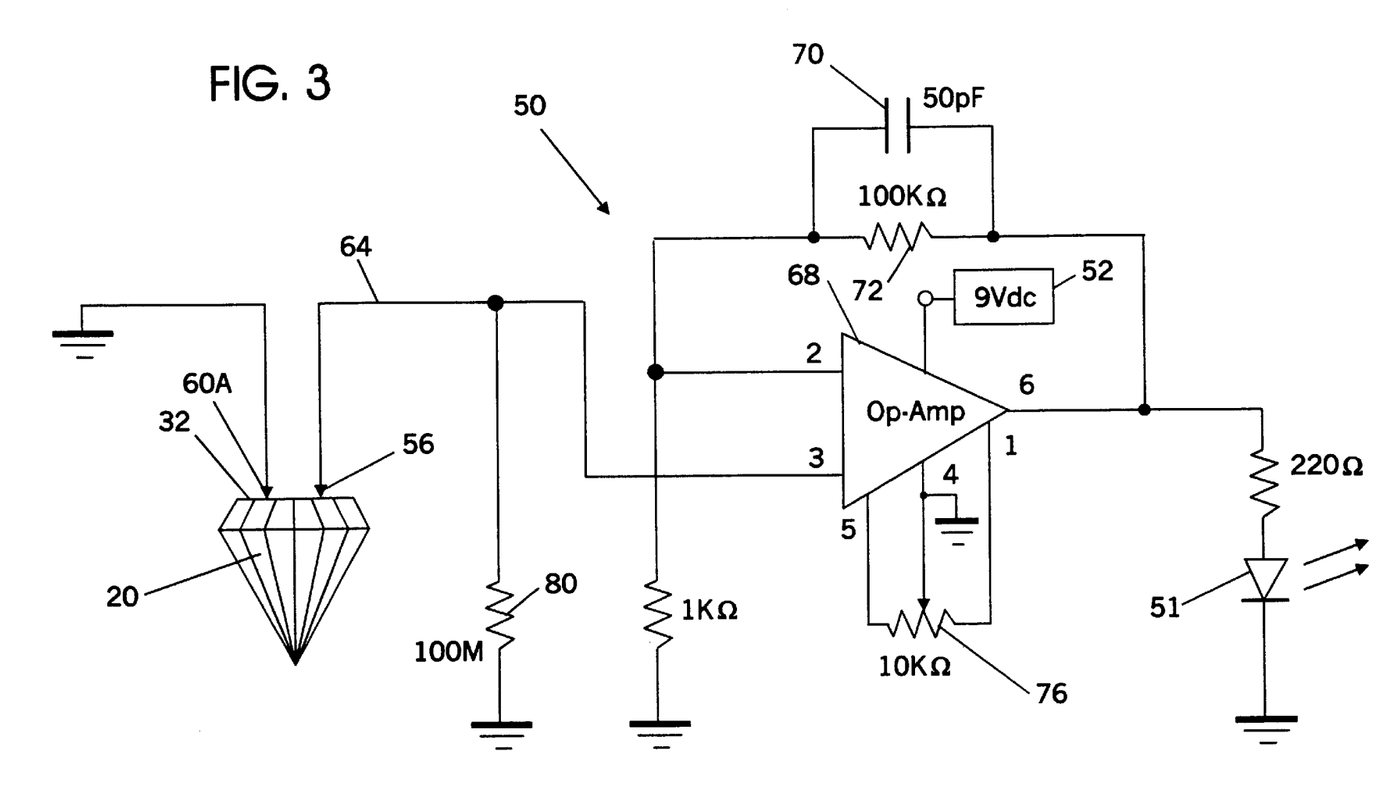
FIG. 3 is a schematic representation of another embodiment incorporating the same circuitry as that of FIG. 2 but with a target gemstone being contacted at its table by a pair of probes.

FIG. 3 illustrates the identical circuit 50 of FIG. 2, but used in conjunction with a target gemstone that is contacted at its table by two probes, probe 56 that connects to the operational amplifier and probe 60A connected to ground.

Figure 4:
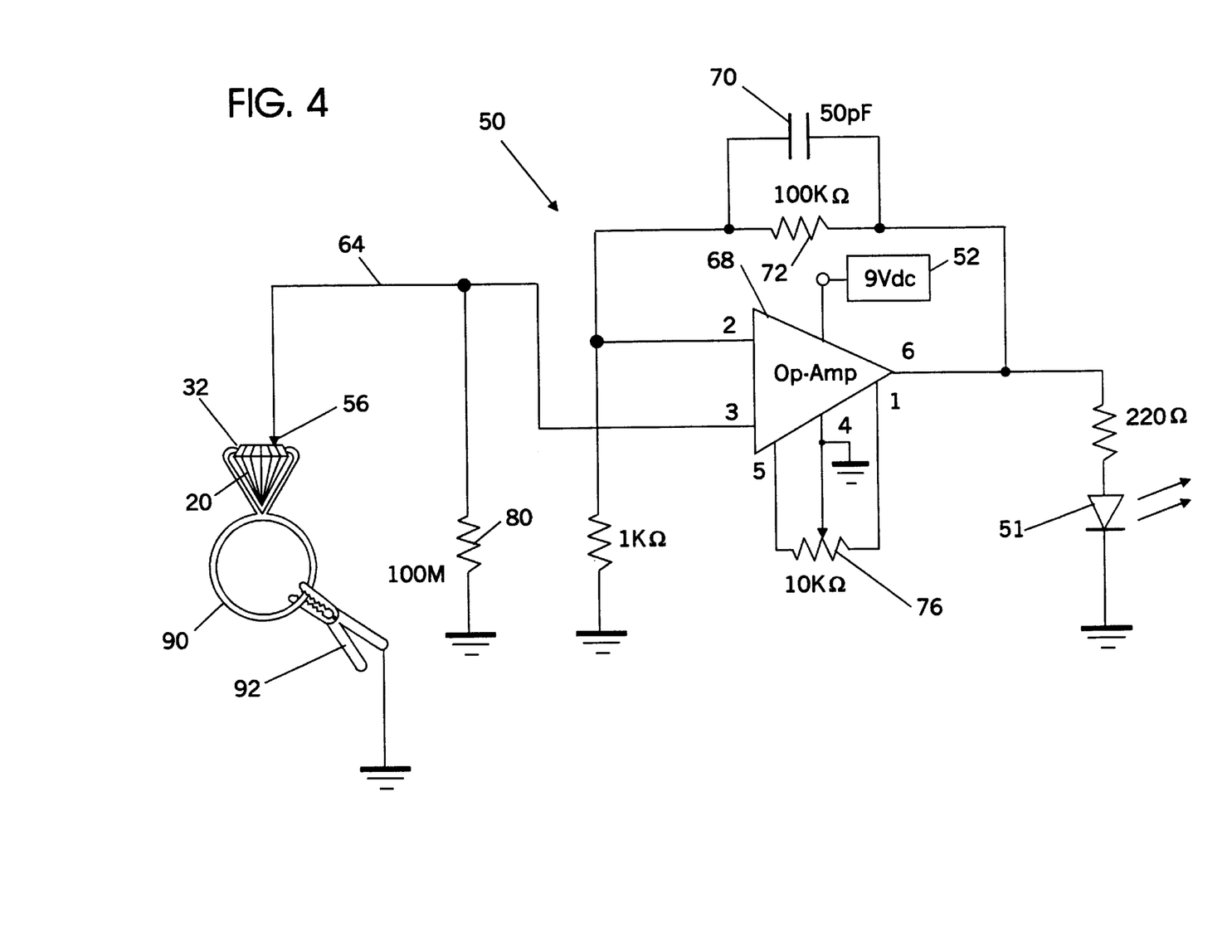
FIG. 4 is a schematic representation of yet another embodiment incorporating the same circuitry as that of FIGS. 2 and 3 but with a target gemstone that is mounted on a ring, and wherein the gemstone is contacted by a single probe and the ring is grounded using, for example, a conductive clip.

FIG. 4 illustrates the identical circuit 50 of FIGS. 2 and 3, but shows a contact arrangement for use with a mounted gemstone. In this embodiment, probe 56 contacts the table of the gemstone in the same manner as in FIGS. 2 and 3. However, the ground connection is made by direct connection to the jewelry mounting the gemstone, for example connection to ring 90 by a conductive clip 92.

While all of the above illustrated embodiments show a contact to the target gemstone at the table of the gemstone, it will be understood that the contacts to the gemstone may be at other points on the gemstone and that the actual points of contact and the spacing between contacts have not been found to be critical.

Figure 5:
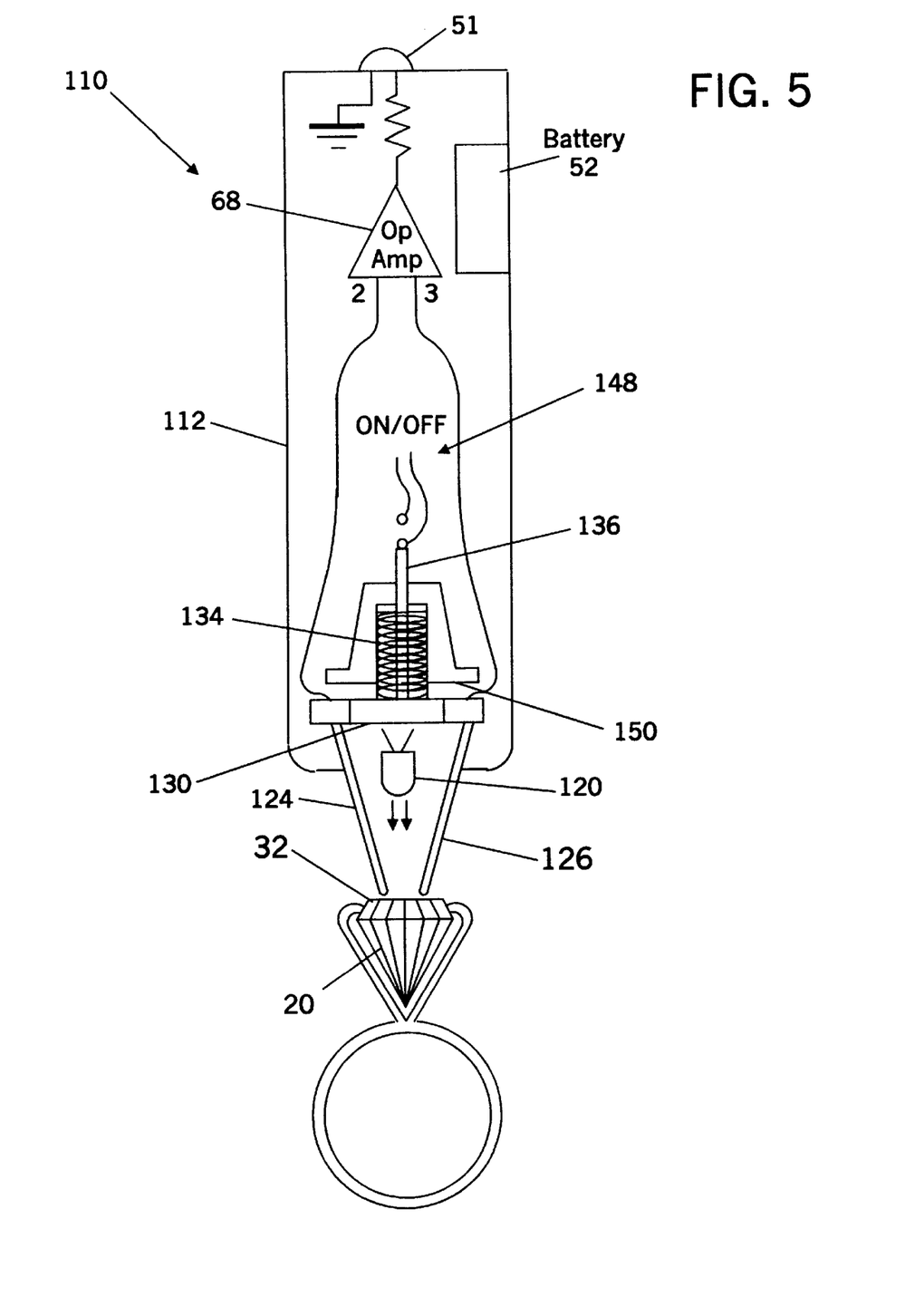
FIG. 5 is a diagrammatic view of a battery operated, hand-held device of the invention for use with either mounted or loose target gemstones.

FIG. 5 illustrates a battery operated, hand-held device 110 that includes an ultraviolet light source. Device 110 includes the same circuit 50 of FIGS. 2–4, with it being understood that the light source and appropriate switching for the light source have been added to the circuit and that only portions of the circuit are shown in FIG. 5 to facilitate illustration. Device 110 includes a cylindrical housing 112 of a suitable size to be easily hand-held while encasing the necessary components. A cylindrical housing on the order of 1.5 inch diameter and 4.5 inch length is acceptable. Housing 112 may be made of any suitable material, for example, an impact resistant plastic. Housing 112 contains a battery 52 contained within a suitable compartment (not shown in detail). Battery 52 supplies energy to both an ultraviolet light source 120 and the remaining components of circuit 50. The electrical contacts to the target gemstone take the form of a pair of probes 124, 126 that extend outwardly from housing 112 and have remote spaced-apart ends for contacting target gemstone 20. This spacing may be on the order of ¹⁄₁₆ to ⅛ inch to permit both probes to contact a relatively small faceted target gemstone.

The other ends of probes 124, 126 are mechanically and electrically connected to a mounting plate 130 that is, in turn, spring-loaded for linear movement along the longitudinal axis of housing 112 against the bias of a spring, for example, a coil torsion spring 134. A longitudinal rod-like member 136 extends from mounting plate 130 and serves to close an on/off switch 148 after displacement on the order of ⅛ inch while, simultaneously, the electrical contacts of mounting plate 130 make electrical connection with a stop plate 150. Thus, pressing probes 124, 126 against the target gemstone actuates the detector circuit, thereby irradiating the target gemstone with ultraviolet energy from light source 120 and producing the output that is a function of the sensed electrical potential across the gemstone.

The output may take the form of a glowing LED 51, an audible output such as a buzzer, or like output. While not shown, it may be desirable to provide a pair of LED's, one indicating "silicon carbide" and the other indicating "other gemstone material".

It has been found that it is advantageous to provide probes 124, 126 with a small amount of flexibility in order to render the probes less brittle and less subject to breakage and also to make it easier for the operator to bring both probe ends into contact with the target gemstone. As mentioned above, suitable probe materials include palladium, brass, and the like, with it being understood that the material is not critical provided it has suitable electrical conductivity.

While the device of FIG. 5 is shown as being used with a mounted target gemstone, the gemstone may be loose and held by the operator's fingers or held by mechanical means such as a four-pronged gem holder customarily used by jewelers and appraisers.

The ultraviolet emitting light source may take the form of a light bulb such as a small halogen bulb or other incandescent bulb. A fully solid state device may be achieved by utilizing a light source in the form of an ultraviolet emitting LED such as a gallium nitride on silicon carbide ultraviolet emitting LED produced by Cree Research, Inc. of Durham, N.C., USA.

Figure 6:
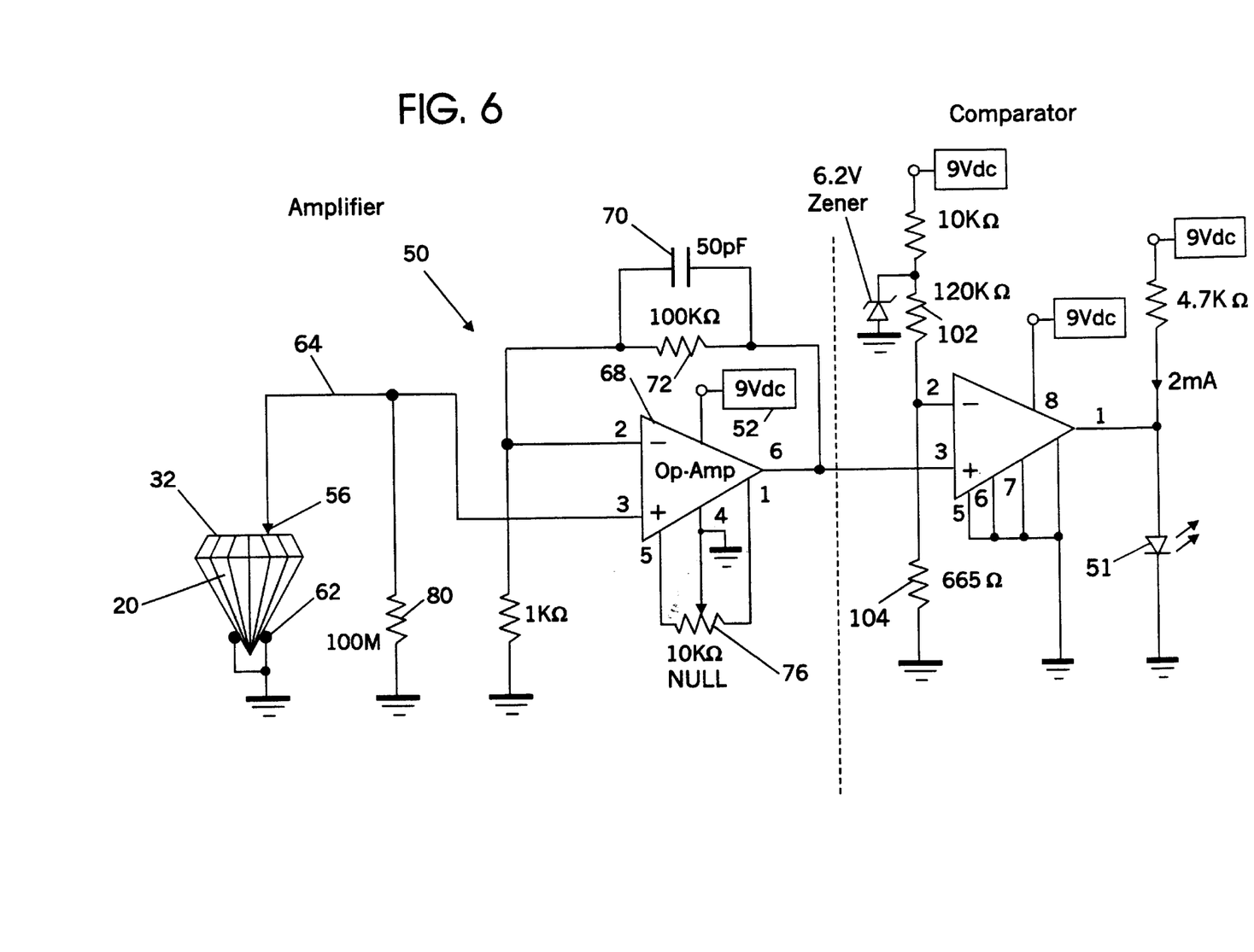
FIG. 6 is a schematic representation of the circuit of FIGS. 2–4 coupled to a comparator circuit.

FIG. 6 illustrates an alternative circuit arrangement that includes a comparator circuit 100 connected to the output (pin 6) of operational amplifier 68 of the previously described circuit 50. Comparator circuit 100 determines, by means of a threshold value established by the ratio between 120 K ohm resistor 102 and 665 ohm resistor 104, a point at which the LED output will light up to a steady state. In the illustrated embodiment, the gain through the amplifier circuit is 100 × and the threshold value established by the comparator circuit is 34 millivolts. Thus, a voltage from the target gemstone at pin 3 of operational amplifier 68 in excess of 0.34 millivolts will be sufficiently great to energize the output LED.

While the invention has been described in connection with certain illustrated embodiments, it will be appreciated That which is claimed is:

1. A device for positively identifying a gemstone as silicon carbide comprising:

means for sensing the electrical potential across a target gemstone that is irradiated with ultraviolet energy; and means for generating an output that is a function of the sensed electrical potential to positively indicate whether the material of the target gemstone is or is not silicon carbide.

2. The device of claim 1 including a light source outputting ultraviolet energy.

3. The device of claim 2 wherein said light source is an incandescent light source.

4. The device of claim 2 wherein said light source is an LED emitting ultraviolet energy.

5. The device of claim 4 wherein said LED is a gallium nitride on silicon carbide ultraviolet emitting LED.

6. A method of positively identifying a gemstone as silicon carbide comprising the steps of:

irradiating a target gemstone with ultraviolet energy;

while the target gemstone is being irradiated with ultraviolet energy, sensing the electrical potential across the target gemstone; and generating an output that is a function of the sensed electrical potential to positively indicate whether the material of the target gemstone is or is not silicon carbide.

7. A device for distinguishing between silicon carbide and diamond gemstones by determining whether a target gemstone having the appearance of diamond produces an electrical potential when irradiated with ultraviolet energy and, therefore, is silicon carbide or, whether the target gemstone produces no appreciable electrical potential when irradiated with ultraviolet energy and, therefore, is diamond, said device comprising:

a light source outputting ultraviolet energy;

a pair of electrical contacts for physically contacting the exterior surface of a target gemstone while the gemstone is positioned for irradiation by ultraviolet energy from the light source; and means connecting to said electrical contacts for generating an output that is a function of the electrical potential across said pair of contacts to positively indicate whether the material of the target gemstone is silicon carbide or diamond.

8. The device of claim 7 wherein said means for generating an output comprises an amplifier circuit for amplifying the voltage across the pair of contacts and using the amplified voltage to drive the output.

9. The device of claim 8 wherein said amplifier circuit variably drives the output proportional in intensity to the signal strength generated by the target gemstone.

10. The device of claim 8 including a comparator circuit between the amplifier circuit and the output, said comparator circuit establishing a threshold value for the amplified signal above which the output is energized and below which the output is not energized.

11. A method of distinguishing between silicon carbide and diamond gemstones comprising determining whether a target gemstone having the appearance of diamond produces an electrical potential when irradiated with ultraviolet energy and, therefore, is silicon carbide, or whether the target gemstone produces no appreciable electrical potential when irradiated with ultraviolet energy and, therefore, is diamond.

12. The method of claim 11 including the steps of:

irradiating a target gemstone with ultraviolet energy;

while the target gemstone is being irradiated with ultraviolet energy, sensing the electrical potential across the target gemstone; and generating an output that is a function of the sensed electrical potential to positively indicate whether the material of the target gemstone is silicon carbide or diamond.

13. A device for positively identifying a gemstone as silicon carbide comprising:

a housing;

a light source mounted by said housing, said light source, when activated, outputting ultraviolet energy;

a pair of electrical contact probes extending from said housing, said electrical contact probes having remote ends that are spaced apart by a distance permitting the remote ends to simultaneously contact the surface of a target gemstone;

the remote ends of the electrical contact probes being positioned in an area that is irradiated with ultraviolet energy when the light source is activated; and means electrically connected to said probes for generating an output that is a function of the electrical potential across said pair of contacts to positively indicate whether the material of the target gemstone is silicon carbide or diamond.

14. The device of claim 13 wherein at least one of said pair of electrical contact probes is mounted to be displaced upon contact with a target gemstone, and said device includes an on-off switch for activating/deactivating said light source in response to displacement of said at least one electrical contact probe.

15. The device of claim 13 wherein said light source is an incandescent light bulb.

16. The device of claim 15 wherein said light source is a quartz halogen bulb.

17. The device of claim 13 wherein said light source is an ultraviolet emitting LED.

18. The device of claim 17 wherein said LED is a gallium nitride on silicon carbide ultraviolet emitting LED.

19. The device of claim 13 wherein said means for generating an output comprises an amplifier circuit for amplifying the voltage across the pair of contacts and using the amplified voltage to drive the output.

20. The device of claim 19 wherein said amplifier circuit variably drives the output proportional in intensity to the signal strength generated by the target gemstone.

21. The device of claim 19 including a comparator circuit between the amplifier circuit and the output, said comparator circuit establishing a threshold value for the amplified signal above which the output is energized and below which the output is not energized.

* * * * *